US012734012B2

(12) United States Patent
Lavallee et al.

(10) Patent No.: US 12,734,012 B2
(45) Date of Patent: Sep. 15, 2026

(54) METHOD FOR REGISTERING A 3D MEDICAL IMAGE WITH A REGISTRATION PHANTOM

(71) Applicant: ECENTIAL ROBOTICS, Gieres (FR)

(72) Inventors: Stéphane Lavallee, Gieres (FR); Clément Vidal, Gieres (FR); Arnaud Pierre, Gieres (FR)

(73) Assignee: ECENTIAL ROBOTICS, Gieres (FR)

( * ) Notice: Subject to any disclaimer, the term of this patent is extended or adjusted under 35 U.S.C. 154(b) by 52 days.

(21) Appl. No.: 18/844,619

(22) PCT Filed: Mar. 29, 2023

(86) PCT No.: PCT/EP2023/058168

§ 371 (c)(1),
(2) Date: Sep. 6, 2024

(87) PCT Pub. No.: WO2023/186996

PCT Pub. Date: Oct. 5, 2023

(65) Prior Publication Data

US 2025/0186159 A1 Jun. 12, 2025

(30) Foreign Application Priority Data

Mar. 29, 2022 (EP) .................................... 22305396

(51) Int. Cl.
*A61B 90/00* (2016.01)

(52) U.S. Cl.
CPC ........ *A61B 90/37* (2016.02); *A61B 2090/363* (2016.02); *A61B 2090/376* (2016.02); *A61B 2090/3966* (2016.02)

(58) Field of Classification Search
CPC ........ A61B 2090/363; A61B 2090/376; A61B 2090/3966
See application file for complete search history.

(56) References Cited

U.S. PATENT DOCUMENTS 5,442,674 A 8/1995 Picard
5,715,918 A 2/1998 Everett
(Continued)

FOREIGN PATENT DOCUMENTS

EP 3361977 B1 1/2020
EP 2676627 B1 7/2021

OTHER PUBLICATIONS

Fucang Jian, et al., "A Simple Method to Calibrate Projection Matri of C-Arm Cone-Beam CT", 2012 International Conference on Biomedical Engineering and Biotechnology, May 28-30, 2012, pp. 682-685.

(Continued)

*Primary Examiner* — Angela M Hoffa
(74) *Attorney, Agent, or Firm* — Thomas | Horstemeyer, LLP

(57) ABSTRACT

The invention relates to a method for registering a 3D medical image obtained by an X-ray imaging system with a registration phantom (1), wherein the registration phantom (1) is positioned onto the patient and comprises a set of radiopaque fiducials (10) having a known position in a coordinate system of said registration phantom (1), said set of radiopaque fiducials not being detectable in the 3D image, the method comprising the steps of: —obtaining at least one 2D X-ray image acquired by the X-ray imaging system wherein at least three radiopaque fiducials (10) of the registration phantom (1) is detectable in each 2D image; —for each of said at least one 2D image, registering the 2D X-ray image with the registration phantom (1) by detecting and determining the position of the at least three radiopaque fiducials (10) in the respective 2D image; —registering each of said at least one 2D X-ray image with the 3D medical image based on the determined position of said radiopaque fiducials in each 2D image and on a projection matrix of the X-ray imaging system, and determining the position of said (Continued)

radiopaque fiducials in the 3D medical image; —registering the registration phantom (1) with the 3D medical image using said positions of the at least three radiopaque fiducials in the 3D medical image.

15 Claims, 6 Drawing Sheets

(56) References Cited

U.S. PATENT DOCUMENTS 7,570,791 B2 8/2009 Frank
8,503,745 B2 * 8/2013 Simon ...................... A61B 6/12 382/128
8,737,708 B2 * 5/2014 Hartmann .............. A61B 34/20 382/128
2011/0071389 A1 * 3/2011 Simon ...................... A61B 6/12 600/426
2012/0201421 A1 * 8/2012 Hartmann ............ A61B 6/5235 382/103
2018/0280092 A1 10/2018 Van Beek
2023/0146679 A1 * 5/2023 Lavallée ................ A61B 34/20 700/259

OTHER PUBLICATIONS

PCT International Search Report in related PCT application No. PCT/EP2023/058168, mailed Jun. 2, 2023.

European Search Report in related EP Application No. 22305396, mailed Sep. 8, 2022.

N. Navab, et al., "Camera-Augmented Mobiel C-arm (CAMC) Application: 3D Reconstruction Using a low-Cost Mobile C-arm", Springer-Verlag Berlin Heidelberg Sep. 19, 1999, pp. 688-698.

* cited by examiner

METHOD FOR REGISTERING A 3D MEDICAL IMAGE WITH A REGISTRATION PHANTOM

CROSS REFERENCE TO RELATED APPLICATIONS

This application is the 35 U.S.C. § 371 national stage application of PCT Application No. PCT/EP2023/058168, filed Mar. 29, 2023, which application claims the benefit of European Application No. EP 22305396.8 filed Mar. 29, 2022, both of which are hereby incorporated by reference herein in their entireties.

TECHNICAL FIELD

The present disclosure relates to a method for registering a 3D medical image with a registration phantom, and an intraoperative surgical system configured to implement such a method.

TECHNICAL BACKGROUND

X-Ray imaging systems are frequently used during medical surgical procedures to provide physicians with image-based information about the anatomical situation and/or the position and orientation of surgical instruments.

Such X-ray imaging systems typically provide two-dimensional (2D) projection images with different structures superimposed along the path of the X-rays.

A typical example of an X-ray imaging system for use in an intra-operative setting is the so-called C-arm used in a mobile or stationary manner and essentially consisting of a base frame on which a C-shaped arm is attached with several intermediate joints allowing moving the C-shaped arm in space along several degrees of freedom.

One end of the C-shaped arm carries an X-ray source and the other end an image detector.

Due to the limited information provided by these 2D images, three-dimensional (3D) imaging techniques have become indispensable over the past decades.

While computer tomography (CT) systems are a well-established class of stationary X-ray imaging systems used for reconstruction of a 3D image in a radiology department, these systems are in general not usable inside the operating room.

Recent years have seen an increasing interest in tomographic reconstruction techniques, also known as cone-beam reconstruction techniques (CBCT), using two-dimensional image detectors.

Special efforts have been made to enable the aforementioned C-arms to provide three-dimensional information by automatically acquiring a set of 2D images of a region of interest and subsequently reconstructing a 3D image based on said cone-beam reconstruction techniques.

Surgical navigation is the application of real-time navigation on intraoperatively acquired fluoroscopic images to achieve the above-mentioned goals.

In view of carrying out said navigation, the tools used during the surgical intervention are equipped with a tracker, e.g. an optical, electromagnetic, ultrasonic, or inertial tracker which is tracked in real time by at least one localization system. Another tracker is mounted onto the patient and is also tracked in real time by the localization system. In this way, the position and orientation of the tools relative to the patient is known in real time.

In view of navigating surgical tools with respect to images acquired by the X-ray imaging device, it is necessary to know the position of said images (or the position the X-ray image detector during acquisition of said images) with respect to the tracker fixed on the patient. To that end, an instrument may be used such as described in [1].

As shown in FIG. 1A, the instrument comprises a registration phantom 1 comprising a plurality of radiopaque fiducials 10 arranged according a known geometry, such that the position of each radiopaque fiducial is known in a coordinate system of the registration phantom. The instrument also comprises a base 2 supporting the registration phantom 1. Preferably, the registration phantom 1 can be removed from the base 2, and a tracker (not shown) can instead be fixed to the base 2 to allow tracking the patient during surgery. The base 2 is rigidly fixed to a patient's bone by at least one percutaneous pin 3, the base 2 and the registration phantom 1 being located outside the patient's body, above the patient's skin S. The dotted line schematically represents the volume V that is reconstructed from 2D X-ray images of the patient. Since said volume V includes not only the region of interest, which is a part of the bone, but also the registration phantom 1, the radiopaque fiducials 10 that are visible in the 3D image allow determining the position of the volume V in the coordinate system of the registration phantom and thus register the 3D image with the registration phantom. Since the tracker is fixed to the same base as the registration phantom, it is thus possible to navigate a surgical instrument within the 3D image.

But sometimes, especially if the patient is obese, the distance between the registration phantom and the region of interest to image is such that said phantom lies outside the reconstructed volume. In that case, traditional methods prove ineffective to register the imaging space with the navigation space.

This situation is illustrated in FIG. 1B. Due to the larger thickness of tissues between the bone B and the skin S, the base 2 and registration phantom 1 are located farther from the bone B. Thus, for a same volume V reconstructed from the 2D X-ray images, the registration phantom 1 is located outside the volume V. Since the radiopaque fiducials 10 are not inside the volume V, it is not possible to determine the position of the volume V in the coordinate system of the registration phantom and thus register the 3D image with the registration phantom.

SUMMARY OF THE DISCLOSURE

It is thus desirable to define a method for registering a 3D medical image obtained by an X-ray imaging system with a registration phantom comprising radiopaque fiducials even if the registration phantom is located relative to the patient such that the radiopaque fiducials are not visible in the 3D medical image.

An object of the present disclosure is thus a method for registering a 3D medical image obtained by an X-ray imaging system with a registration phantom, wherein the registration phantom is positioned onto the patient and comprises a set of radiopaque fiducials having a known position in a coordinate system of said registration phantom, said set of radiopaque fiducials not being detectable in the 3D image, the method comprising the steps of:

- obtaining at least one 2D X-ray image acquired by the X-ray imaging system wherein at least three radiopaque fiducials of the registration phantom are detectable in each 2D image;

for each obtained 2D X-ray image, registering the 2D X-ray image with the registration phantom by detecting and determining the position of the at least three radiopaque fiducials in the respective 2D image;

determining the position of each of said at least three radiopaque fiducials relative to the 3D medical image based on the determined position of said fiducials in each 2D X-ray image and on a projection matrix of the X-ray imaging system;

registering the registration phantom with the 3D medical image using said at least three radiopaque fiducials.

In preferred embodiments, determining the position of each of said at least three radiopaque fiducials relative to the 3D medical image comprises using the projection matrix to compute, for each 2D X-ray image, the back-projection rays from the determined 2D positions of said radiopaque fiducials in the 2D X-ray image.

In some embodiments, the 3D medical image is reconstructed from a set of 2D images acquired by the X-ray imaging system and the at least one 2D image is selected from said set of 2D images.

In other embodiments, the 3D medical image is reconstructed from a set of 2D images acquired by the X-ray imaging system and the 2D images wherein at least three radiopaque fiducials of the registration phantom are detectable are acquired with the X-ray imaging system after reconstructing the 3D medical image.

In other embodiments, wherein the 3D medical image is reconstructed from a set of 2D images acquired by the X-ray imaging system and the 2D images are acquired with the X-ray imaging system before reconstructing the 3D medical image.

In some embodiments, a single 2D X-ray image in which at least three radiopaque fiducials of the registration phantom are detectable is obtained.

Determining the position of each of said at least three radiopaque fiducials relative to the 3D medical image may thus comprise determining the position of each radiopaque fiducial on a respective back-projection ray based on the known position of said radiopaque fiducials in the coordinate system of the registration phantom.

In other embodiments, at least two 2D X-ray images in which at least three radiopaque fiducials of the registration phantom are detectable are obtained.

Back-projection rays may thus be computed for each radiopaque fiducial for each of the at least two 2D X-ray images, and the position of each radiopaque fiducial relative to the 3D medical image may be determined from an intersection between the respective back-projection rays computed for each 2D X-ray image.

Another object is an intraoperative surgical system comprising:

a registration phantom comprising a set of radiopaque fiducials having a known position in a coordinate system of said registration phantom, said registration phantom being adapted to be positioned onto a patient, an X-ray imaging system configured to acquire a set of 2D X-ray images and to reconstruct a 3D medical image from said set of 2D X-ray images, a computer system configured to:

(i) obtain at least one 2D X-ray image acquired by the X-ray imaging system wherein at least three radiopaque fiducial (10) of the registration phantom (1) is detectable in each 2D image;

(ii) for each obtained 2D X-ray image, register the 2D X-ray image with the registration phantom by detecting and determining the position of the at least three radiopaque fiducials in the respective 2D image;

(iii) determine the position each of said at least three radiopaque fiducials relative to the 3D medical image based on the determined position of said radiopaque fiducials in each 2D X-ray image and on a projection matrix of the X-ray imaging system;

(iv) register the registration phantom with the 3D medical image using said at least three radiopaque fiducials.

In preferred embodiments, the X-ray imaging system is a motorized C-arm.

In some embodiments, the system further comprises a radiotransparent base configured to be attached to the patient's anatomy, said base comprising a fixation system for removably attaching the registration phantom to the base.

The system may further comprise a localization system and at least one tracker adapted to be tracked by the localization system, the base comprising a fixation system for removably attaching the tracker to the base.

BRIEF DESCRIPTION OF THE FIGURES

Further features and advantages of the method and the system will be apparent from the following detailed description, based on the appended drawings, in which.

For sake of clarity, the figures are not necessarily drawn to scale.

The reference signs identical from one figure to another one designate the same elements or elements having the same function. Thus, these elements may not be described in detail again.

DETAILED DESCRIPTION OF EMBODIMENTS

The registration method is carried out thanks to a computer system which comprises at least one processor configured to implement algorithms, at least one data storage device, a communication module and at least one user interface.

The intraoperative surgical system also comprises an X-ray imaging system configured to reconstruct a 3D image from a set of 2D X-ray images, in particular by CBCT.

In some embodiments, the computer system may be the control unit of the X-ray imaging system.

In other embodiments, the computer system may be coupled to the control unit of the X-ray imaging system, so as to receive 2D and/or 3D images from the X-ray imaging system. The computer system may also send commands to the control unit of the X-ray imaging system to acquire additional 2D X-ray images, in particular when such additional images are necessary to perform the registration of the 3D image with the registration phantom, as will be described below.

In other embodiments, the computer system may not be coupled to the control unit of the X-ray imaging system. In such case, all the images necessary for the implementation of the method are acquired independently by an X-ray imaging system and recorded on a suitable support, and the computer system receives said images from the support to perform the registration.

The intraoperative surgical system may also include a localization system adapted to track in real time trackers attached to the patient and to at least one surgical tool.

Registration Phantom

Figure 2:
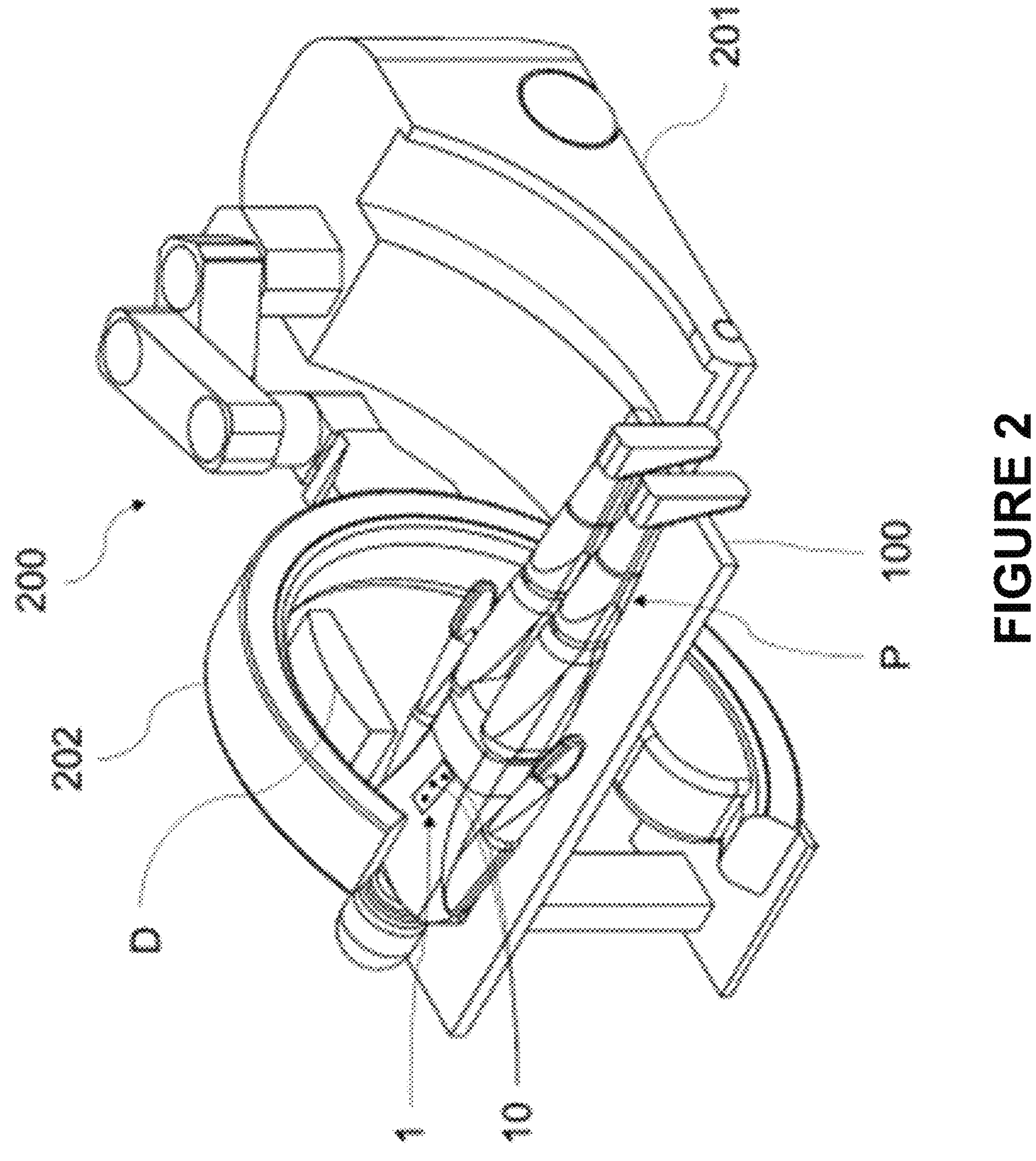
FIG. 2 represents a surgical scene comprising an intraoperative X-ray imaging system and a patient lying on an operating table.

As shown in FIG. 2, at the beginning of a surgical intervention, a patient P lies on an operating table 100.

A registration phantom 1 is placed onto the patient. Preferably, the placement of the registration phantom is done without any surgical step, for example by using an adhesive to attach the registration phantom to the patient's skin, or by attaching the registration phantom to a device already implanted into a patient's bone for another purpose, such as the base intended to attach a tracker to the bone.

Figure 1A:
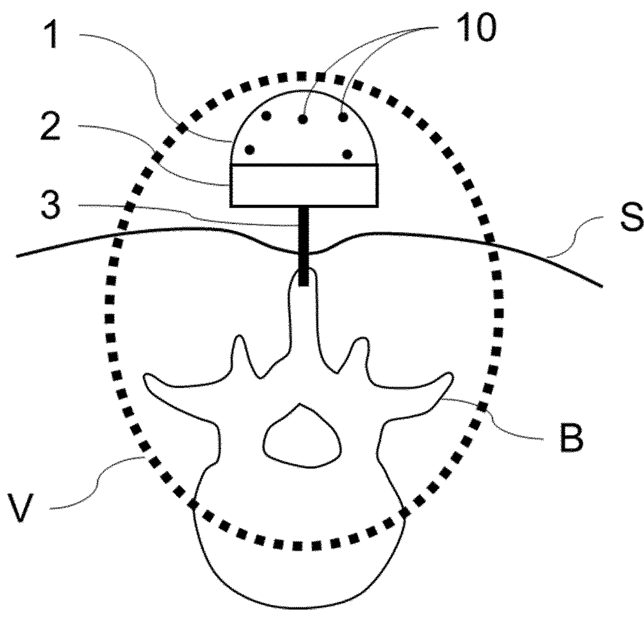
FIG. 1A is a schematic view of a registration phantom close enough to the region of interest to allow registering a 3D image of the region of interest with the coordinate system of the registration phantom by detecting the radiopaque fiducials of the registration phantom in the 3D image.
Figure 1B:
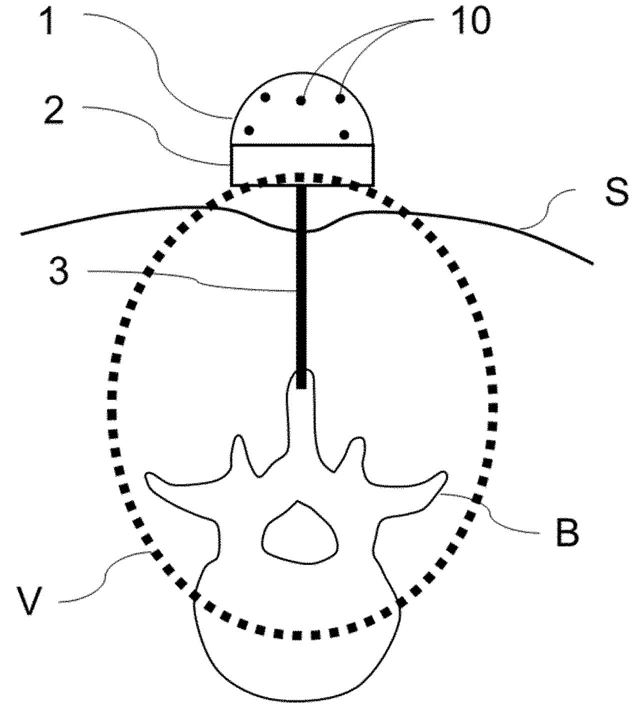
FIG. 1B is a schematic view of a registration phantom too far from the region of interest to allow registering a 3D image of the region of interest with the coordinate system of the registration phantom by detecting radiopaque fiducials of the registration phantom in the 3D image.

As shown in FIG. 1B, the registration phantom 1 comprises at least three radiopaque fiducials 10. Each fiducial has a known position in a 3D coordinate system of the registration phantom.

Each fiducial may be a ball-shaped or a needle-shaped piece of radiopaque material, such as steel, stainless steel, or zircon, and whose dimensions are known by any methods available to the skilled person. The fiducials are embedded in or supported by a support made of a substantially radiotransparent material. In this way, when a 2D X-ray image of the registration phantom is acquired, the fiducials are visible in the image whereas the support is substantially not visible, or at least does not hinder the detection of the fiducials in the 2D X-ray image.

The registration phantom is attached to the patient above the patient's skin, i.e. outside the patient's body.

Various ways of non-invasive or minimally-invasive fixation of the registration phantom to the patient may be used.

In some embodiments, the registration phantom may be fixed to the patient's skin by an adhesive. Although such a fixation does not provide a strictly rigid attachment to a patient's bone due to the presence of soft tissues interposed the registration phantom and the bone, it may be considered that, if the registration phantom is sufficiently close to the bone, for example just above the bone, the fixation is sufficiently rigid to provide a reasonable accuracy of the registration.

In other embodiments, the registration phantom may be fixed to a patient's bone by at least one percutaneous pin.

Preferably, the registration phantom may be attached to a base 2 of a modular device that is provided for attachment of a tracker to the patient. In such a way, the fixation of the registration phantom does not require any surgical step, but simply benefits from the base that is attached to the patient for navigation of a surgical tool.

Said modular device advantageously comprises:

the registration phantom 1;

the base 2, which is made of a substantially radiotransparent material, said base being configured to be rigidly secured to a patient, for example by percutaneous pins;

a tracker (not shown) adapted to be tracker by a localization system.

The base comprises a fixation system adapted to rigidly attach the registration phantom and the tracker to the base. Preferably, the fixation system allows removing the registration phantom and/or the tracker from the base. Said fixation system is preferably designed to allow a reproducible fixation of the registration phantom and/or the tracker, i.e. to provide a same position of the registration phantom and/or the tracker relative to the base over time.

Since the registration phantom and the tracker are not used in the same steps of the surgical procedure, the base may comprise a common fixation system for interchangeably attaching the tracker and the registration phantom to the base.

X-Ray Imaging System

The X-ray imaging system 200 comprises at least one X-ray source (not visible in FIG. 2) and at least one X-ray image detector D.

The X-ray imaging system is configured to produce at least one 2D X-ray image that is the result of a conical projection of a patient's anatomy, wherein the tip of the cone is approximately the central point of the X-ray source and the basis of the cone is approximately the portion of the X-ray image detector that is reached by X-ray beams that have been collimated in a given shape and orientation.

For example, the X-ray imaging system may be a conventional C-arm, or any Cone-Beam Computed Tomography (CBCT) such as the SURGIVISIO device (eCential Robotics, Giéres, France), or VISON FD VARIO 3D (Ziehm), CIOS SPIN MOBILE 3D (Siemens), AIRO (Stryker), LOOP-X (Brainlab), O-ARM (Medtronic).

A CBCT-capable system has a mobile X-ray source and a mobile X-ray image detector, wherein the X-ray source and the X-ray image detector have motorized motions, moving together or independently. A CBCT system can have a C-arm shape or an O-arm shape. It can be used to acquire a set of 2D X-ray images over approximately 180° of orbital rotation that can be combined with translations and from which a 3D image can be reconstructed using tomography or tomosynthesis algorithms.

The C-shaped arm may comprise motors allowing movement horizontally, vertically and around the swivel axes, so that 2D X-ray images of the patient are produced from almost any angle. Each motor is associated to an encoder that provides at any time the relative position of the X-ray imaging system with respect to a reference position. When a 2D X-ray image is acquired, the corresponding position of the imaging system is recorded. Thus, each 2D image is recorded in a 3D coordinate system of the X-ray imaging system.

The X-ray imaging system 200 advantageously has a mobile base 201 allowing displacing the C-arm 202 in the operating room. Said mobile base may comprise control switches (not illustrated), such as a power switch, an emergency button and the like.

The acquisition of the X-ray images and the activation of the motors of the C-arm, is controlled by a control unit of the X-ray imaging system. Said control unit comprises at least one processor configured to implement algorithms, at least one data storage device, a communication module and at least one user interface.

Said control unit may be embedded in the mobile base 201 of the X-ray imaging system or in a separate cart.

Reconstruction of the 3D Image

As shown in FIG. 2, the intraoperative X-ray imaging system 200 is brought along the operating table 100 and positioned relative to a predetermined region of interest of the patient so as to be able to acquire a 3D volume of said region. The region of interest may be an anatomical structure of the patient, such as a bone or a plurality of bones, or a part of an anatomical structure.

The 3D volume is acquired intraoperatively with the X-ray imaging system through the acquisition of a set of 2D X-ray images along an acquisition path, typically evolving at least a full orbital motion.

The set of 2D images may comprise up to several hundreds of 2D images.

Tomography is then used to reconstruct a 3D volume of the region of interest from the plurality of acquired 2D X-ray images.

The reconstructed 3D volume is defined as the intersection of all the conical projections corresponding to the set of 2D images. In order to maximize the size of the 3D image of the region of interest, the acquisition of the 2D X-ray images is preferably done with an acquisition path minimizing the distance between the image detector and the patient's body. Such an acquisition path also has the advantage of moving the X-ray source away from the patient's body, which allows reducing the X-ray dose received by the patient.

However, if, as shown in FIG. 1B, the registration phantom is too far from the region of interest, it is not included in the reconstructed 3D volume. This situation may occur in particular when the patient suffers from obesity, in which case the distance between the registration phantom and the region of interest to image is so large that said phantom lies outside the reconstructed volume. Such a situation may also occur if the workflow of the surgical intervention requires that the registration phantom be placed in another position distant from the region of interest; this may happen, for example, if the registration phantom is not removable and has to be kept on the patient during the whole surgical procedure and the surgeon requests that the registration phantom be placed in a position that does not hinder the surgical gesture.

The registration of the 3D image with the registration phantom is thus carried out as follows.

Registration of the 3D Image with the Registration Phantom

At least one 2D X-ray image is acquired by the X-ray imaging system such that at least three radiopaque fiducials of the registration phantom are detectable in each 2D image.

In one embodiment, more than one 2D X-ray image, in which at least three radiopaque fiducials are detectable, is acquired. Indeed, the more 2D X-ray images are acquired, the better the accuracy of the registration of the 3D image with the registration phantom will be.

In an advantageous embodiment, the at least three radiopaque fiducials detectable in the acquired 2D X-ray images correspond to the same radiopaque fiducials of the registration phantom. In other words, in each acquired 2D X-ray images, the same at least three radiopaque fiducials are detectable.

In these 2D X-ray images, the region of interest is also visible. The region of interest thus forms a common feature between the 2D X-ray images and the 3D image, that will allow the registration.

In some embodiments, said at least one 2D X-ray image is selected from the set of 2D X-ray images used for the reconstruction. This allows avoiding the acquisition of additional 2D X-ray images and thus avoiding increasing the X-ray dose received by the patient. In order to maximize the accuracy of the method, said 2D X-ray images may be selected so as to maximize the number of radiopaque fiducials visible in each 2D X-ray image. Preferably, said 2D X-ray images may also be chosen to correspond to sufficiently different angles of incidence of the X-rays.

In other embodiments, said at least one 2D X-ray image is acquired with the X-ray imaging system before reconstructing the 3D medical image. In such case, the position of the X-ray source and image detector for each image acquisition is specifically chosen so as to ensure that the radiopaque fiducials of the registration phantom will be visible in each of said 2D X-ray images.

In other embodiments, said at least one 2D X-ray image is acquired with the X-ray imaging system after reconstructing the 3D medical image. In such case, the position of the X-ray source and image detector for each image acquisition is specifically chosen so as to ensure that the radiopaque fiducials of the registration phantom will be visible in each of said 2D X-ray images. Carrying out this additional acquisition after reconstructing the 3D medical image allows exposing the patient to an additional X-ray dose only if the 2D X-ray images already acquired do not allow implementing the registration method.

Figure 3:
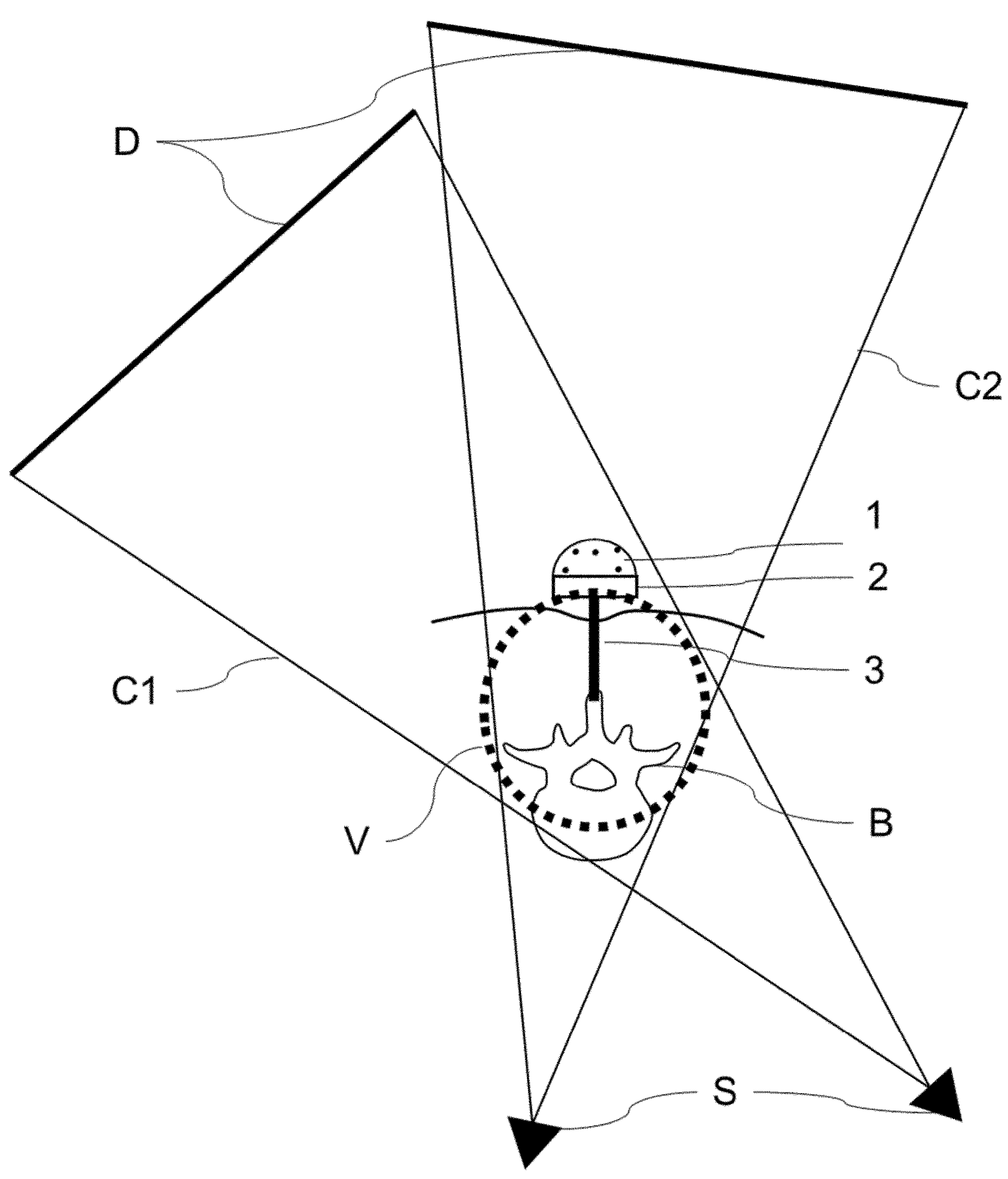
FIG. 3 schematically illustrates the acquisition of two 2D X-ray images in which the radiopaque fiducials of the registration phantom are visible.

FIG. 3 schematically illustrates the acquisition of such 2D X-ray images. Each 2D X-ray image is the result of a conical projection of the patient's anatomy, wherein the tip of each cone C1, C2 is approximately the central point of the X-ray source S and the base of the cone is approximately the portion of the X-ray image detector D that is reached by X-ray beams that have been collimated in a given shape and orientation.

The method then comprises, for each 2D image, registering the 2D X-ray image with the registration instrument by detecting and determining the position of the radiopaque fiducials in the respective 2D image.

Figure 4:
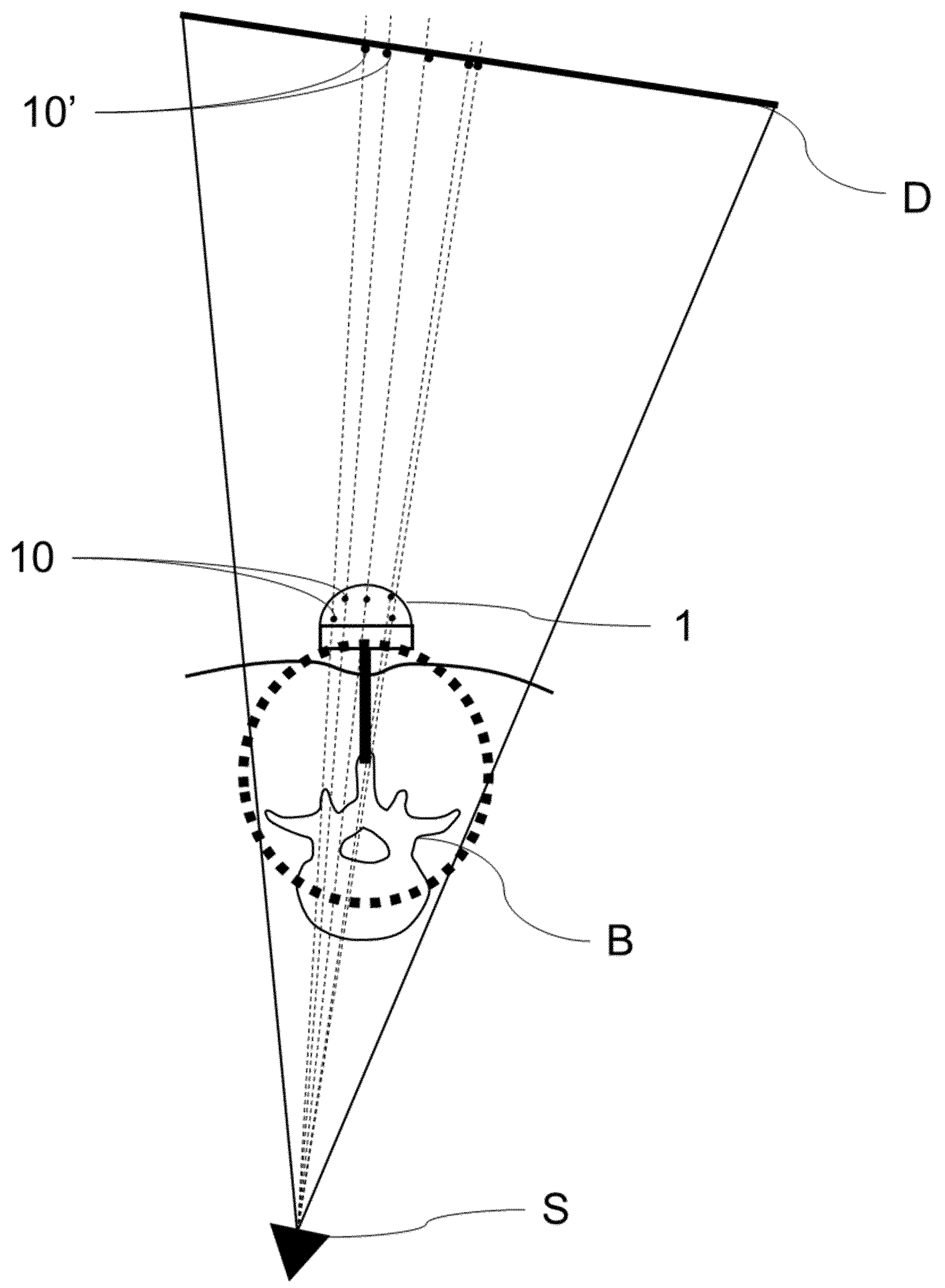
FIG. 4 schematically illustrates the registration of a 2D X-ray image with the registration phantom.

FIG. 4 schematically illustrates said registration step for one 2D X-ray image.

The dotted lines represent the direction of projection of each radiopaque fiducial 10 onto the image detector D, to form a respective spot 10' visible in the 2D X-ray image.

The detection of the radiopaque fiducials in the 2D X-ray image allows determining the position of said 2D X-ray image in the coordinate system of the registration phantom.

The method then comprises determining the position of each of the at least three radiopaque fiducials relative to the 3D image based on the determined position of said radiopaque fiducials in each 2D X-ray image and a projection matrix of the X-ray imaging system.

The projection matrix takes into account the geometric model of the X-ray imaging system and defines the transformation of a 3D point of the 3D volume to a 2D-pixel of a 2D X-ray image. This projection matrix can be provided by the manufacturer of the X-ray imaging system, or estimated with a calibration method.

A common technique for calibrating an X-ray imaging system consists in using a well-defined calibration phantom that allows precise determination of the entire projection geometry for each image take throughout a scan, such that the predicted radiopaque fiducials projections based on that geometry and a model of the phantom optimally match the locations of the radiopaque fiducials identified in the image. More details can be found in [2][3][4][5].

More particularly, the projection matrix is used to compute, for each 2D X-ray image, the back-projection rays from the determined 2D positions of said radiopaque fiducials in the 2D X-ray image.

In the embodiment where only one 2D X-ray image is acquired, those back-projection rays are combined with the known relationship between the at least three detectable radiopaque fiducials, such as their relative distance, to determine the coordinates of the radiopaque fiducials in the 3D volume.

Figure 5:
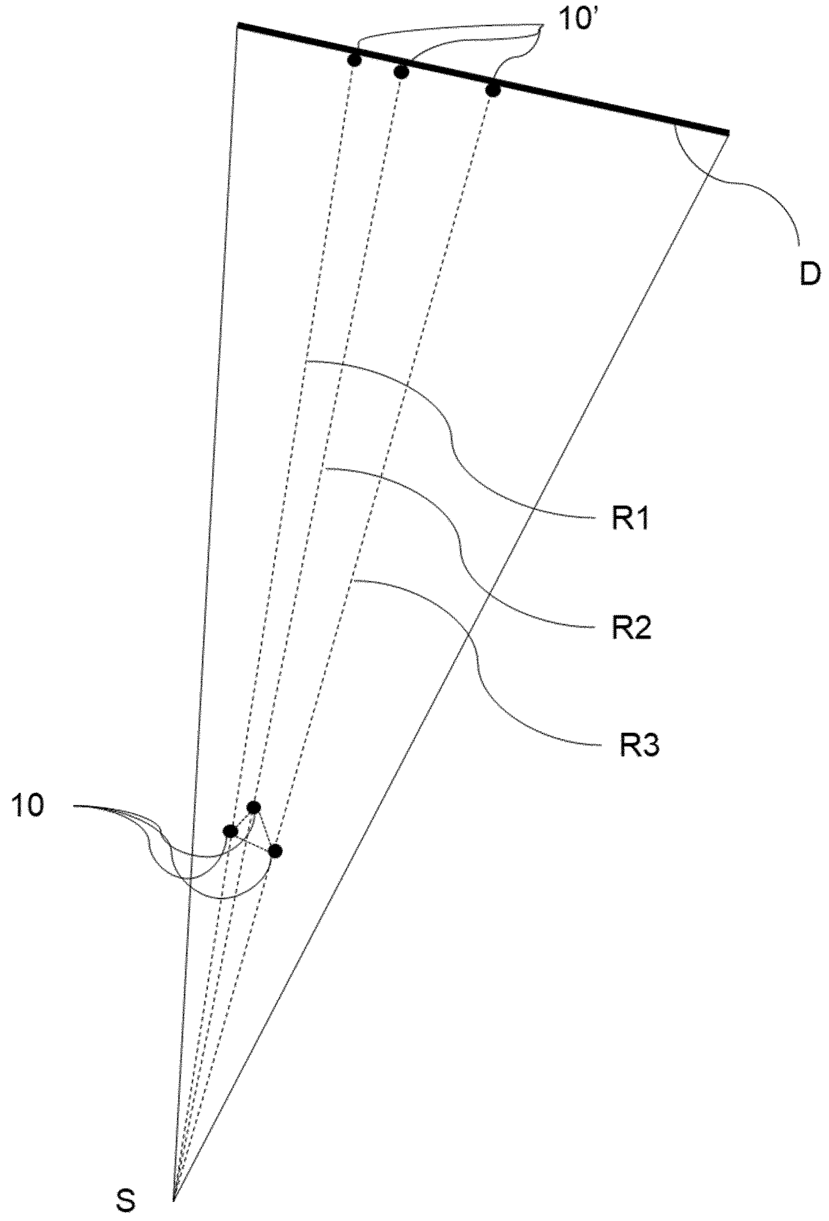
FIG. 5 schematically illustrates a method for determining the position of the radiopaque fiducials relative to the 3D image based on a single 2D X-ray image.

FIG. 5 illustrates three radiopaque fiducials 10 and the corresponding spots 10' on the detector D, that are detectable in the 2D X-ray image. Each back-projection ray R1, R2, R3 connects a respective spot 10' and the X-ray source S. The position of the radiopaque fiducials 10 on the rays R1-R3 is unknown but it can be determined based on their known relative relationship, by searching which position of the fiducials 10 on the rays R1-R3 meets said known relationship.

In the embodiment where at least two 2D X-ray images are acquired, for each of the at least three radiopaque fiducials, an "optimal" intersection between the respective back-projection rays of each radiopaque fiducial from each of the 2D X-ray images is determined. This optimal intersection corresponds to the coordinates of the radiopaque fiducial in the 3D volume. The more 2D X-ray images are used the better the accuracy. This optimal intersection can be obtained using a minimization of the sum of the squares of the distances between the back-projection rays or by other methods.

Figure 6:
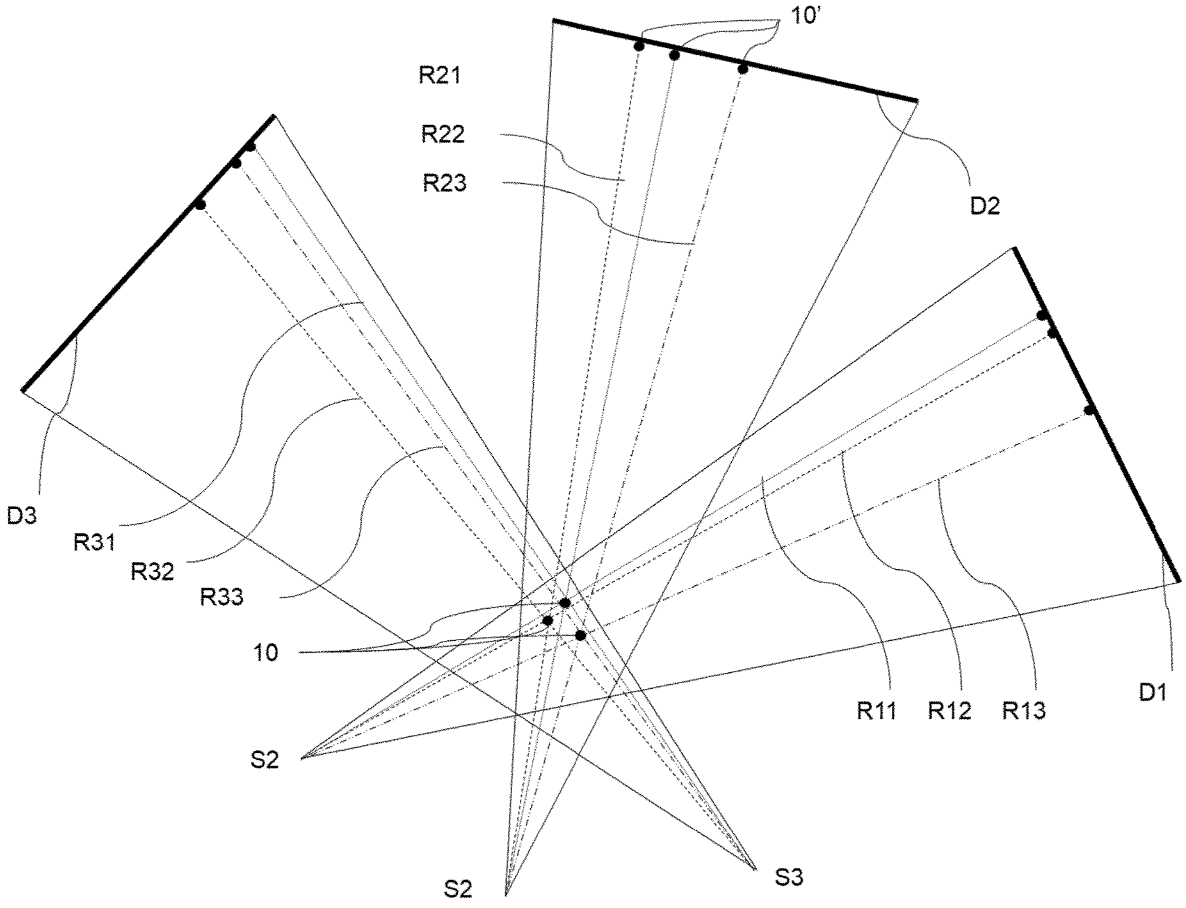
FIG. 6 schematically illustrates a method for determining the position of the radiopaque fiducials relative to the 3D image based on three 2D X-ray images.

FIG. 6 illustrates an embodiment using three 2D X-ray images. The same three radiopaque fiducials 10 are used and the corresponding spots 10' are detectable in the three 2D X-ray images (the position of the detector during the acquisition of each 2D X-ray image is designated by D1, D2, D3 and the respective position of the X-ray source is designated by S1, S2, S3. For each image i (i being an integer comprised between 1 and 3), back-projection rays Ri1, Ri2, Ri3 connect a respective spot 10' on the detector Di and the X-ray source Si. The position of the radiopaque fiducials on the rays Ri1-Ri3 is unknown but the position of each radiopaque fiducial j (j being an integer comprised between 1 and 3) can be determined by the intersection of the rays R1$j$, R2$j$ and R3$j$.

Other methods can be used to determine, using the back-projection rays computed from the projection matrix, the coordinates of the at least three radiopaque fiducials in the 3D volume. It is also possible to combine the two previously described methods.

The method then comprises the registration of the 3D image with the registration phantom. This registration is made via the at least three radiopaque fiducials, whose position is known with respect to both the registration phantom and the 3D image. It is thus possible to establish a correspondence between the 3D image and the coordinate system of the registration phantom.

REFERENCES

[1] US 2018/0280092

[2]N. Navab, M. Mitschke, O. Schutz, "Camera-augmented Mobile C-arm Application: 3D Reconstruction using a Low-cost Mobile C-arm". Proceedings of International Conference on Medical Image Computing and Computer Assisted Intervention. 1999, 688-69 7.

[3] Jia, Fucang & Li, Yuan & Xu, Hongwei & Zhang, Xiaodong & Hu, Qingmao. (2012). A Simple Method to Calibrate Projection Matrix of C-Arm Cone-Beam CT. 682-685. 10.1109/iCBEB.2012.41.

[4]U.S. Pat. No. 5,715,918

[5]U.S. Pat. No. 5,442,674

The invention claimed is:

1. A method for registering a 3D medical image obtained by an X-ray imaging system with a registration phantom, wherein the registration phantom is positioned onto the patient and comprises a set of radiopaque fiducials having a known position in a coordinate system of said registration phantom, said set of radiopaque fiducials not being detectable in the 3D image, the method comprising:

obtaining at least two 2D X-ray images acquired by the X-ray imaging system wherein at least three radiopaque fiducials of the registration phantom are detectable in each 2D image;

for each obtained 2D X-ray image, registering the 2D X-ray image with the registration phantom by detecting and determining the position of the at least three radiopaque fiducials in the respective 2D image;

computing for each 2D X-ray image, back-projection rays from the determined positions of said radiopaque fiducials in the respective 2D X-ray image based on a projection matrix of the X-ray imaging system;

determining the position of each of said at least three radiopaque fiducials relative to the 3D medical image from an intersection between the respective back-projection rays computed for each 2D X-ray image, thereby registering the registration phantom with the 3D medical image.

2. The method of claim 1, wherein the 3D medical image is reconstructed from a set of 2D images acquired by the X-ray imaging system and the at least two 2D X-ray images wherein at least three radiopaque fiducials of the registration phantom are detectable in each 2D image are selected from said set of 2D images.

3. The method of claim 1, wherein the 3D medical image is reconstructed from a set of 2D images acquired by the X-ray imaging system, and obtaining the at least two 2D X-ray images wherein at least three radiopaque fiducials of the registration phantom are detectable in each 2D image is implemented in an additional image acquisition after reconstructing the 3D medical image.

4. The method of claim 1, wherein the 3D medical image is reconstructed from a set of 2D images acquired by the X-ray imaging system and the at least two 2D X-ray images wherein at least three radiopaque fiducials of the registration phantom are detectable in each 2D image are acquired with the X-ray imaging system before reconstructing the 3D medical image.

5. The method of claim 1, wherein a single 2D X-ray image in which at least three radiopaque fiducials of the registration phantom are detectable is obtained.

6. The method of claim 5, wherein determining the position of each of said at least three radiopaque fiducials relative to the 3D medical image comprises using the projection matrix to compute, for each 2D X-ray image, back-projection rays from the determined positions of said radiopaque fiducials in the 2D X-ray image, and wherein determining the position of each of said at least three radiopaque fiducials relative to the 3D medical image comprises determining the position of each radiopaque fiducial on a respective back-projection ray based on the known position of said radiopaque fiducials in the coordinate system of the registration phantom.

7. An intraoperative surgical system comprising:

a registration phantom comprising a set of radiopaque fiducials having a known position in a coordinate system of said registration phantom, said registration phantom being adapted to be positioned onto a patient, an X-ray imaging system configured to acquire a set of 2D X-ray images and to reconstruct a 3D medical image from said set of 2D X-ray images, and a computer system configured to:

(i) obtain at least two 2D X-ray images acquired by the X-ray imaging system wherein at least three radiopaque fiducials of the registration phantom are detectable in each 2D image;

(ii) for each obtained 2D image, register the 2D X-ray image with the registration phantom by detecting and determining the position of the at least three radiopaque fiducials in the respective 2D image;

(iv) compute for each 2D X-ray image, back-projection rays from the determined positions of said radiopaque fiducials in the respective 2D X-ray image based on a projection matrix of the X-ray imaging system;

(iv) determine the position of each of said at least three radiopaque fiducials relative to the 3D medical image from an intersection between the respective back-projection rays computed for each 2D X-ray image, thereby registering the registration phantom with the 3D medical image.

8. The system of claim 7, wherein the X-ray imaging system is a motorized C-arm.

9. The system of claim 7, further comprising a radiotransparent base configured to be attached to the patient's anatomy, said base comprising a fixation system for removably attaching the registration phantom to the base.

10. The system of claim 7, further comprising a localization system and at least one tracker adapted to be tracked by the localization system, the base comprising a fixation system for removably attaching the tracker to the base.

11. A method for registering a 3D medical image obtained by an X-ray imaging system with a registration phantom, wherein the registration phantom is positioned onto the patient and comprises a set of radiopaque fiducials having a known position in a coordinate system of said registration phantom, said set of radiopaque fiducials not being detectable in the 3D image, the method comprising:

obtaining one 2D X-ray image acquired by the X-ray imaging system wherein at least three radiopaque fiducials of the registration phantom are detectable in said 2D X-ray image;

registering said 2D X-ray image with the registration phantom by detecting and determining the position of the at least three radiopaque fiducials in the respective 2D image;

computing for said 2D X-ray image, back-projection rays from the determined positions of said radiopaque fiducials in said 2D X-ray image based on a projection matrix of the X-ray imaging system;

determining the position of each radiopaque fiducial on a respective back-projection ray based on the known position of said radiopaque fiducials in the coordinate system of the registration phantom, thereby determining the position of each radiopaque fiducial relative to the 3D medical image, thereby registering the registration phantom with the 3D medical image.

12. The method of claim 11, wherein the 3D medical image is reconstructed from a set of 2D images acquired by the X-ray imaging system and the 2D X-ray image wherein at least three radiopaque fiducials of the registration phantom are detectable is selected from said set of 2D images.

13. The method of claim 11, wherein the 3D medical image is reconstructed from a set of 2D images acquired by the X-ray imaging system and obtaining the 2D X-ray image wherein at least three radiopaque fiducials of the registration phantom are detectable is implemented in an additional image acquisition after reconstructing the 3D medical image.

14. The method of claim 11, wherein the 3D medical image is reconstructed from a set of 2D images acquired by the X-ray imaging system and the 2D X-ray image wherein at least three radiopaque fiducials of the registration phantom are detectable is acquired with the X-ray imaging system before reconstructing the 3D medical image.

15. A method for registering a 3D medical image obtained by an X-ray imaging system with a registration phantom, wherein the registration phantom is positioned onto the patient and comprises a set of radiopaque fiducials having a known position in a coordinate system of said registration phantom, said set of radiopaque fiducials not being detectable in the 3D image, the method comprising:

obtaining at least one 2D X-ray image acquired by the X-ray imaging system wherein at least three radiopaque fiducials of the registration phantom are detectable in each 2D image;

for each obtained 2D X-ray image, registering the 2D X-ray image with the registration phantom by detecting and determining the position of the at least three radiopaque fiducials in the respective 2D image;

determining the position of each of said at least three radiopaque fiducials relative to the 3D medical image based on the determined position of each of said radiopaque fiducials in each 2D X-ray image and on a projection matrix of the X-ray imaging system, thereby registering the registration phantom with the 3D medical image, wherein the 3D medical image is reconstructed from a set of 2D images acquired by the X-ray imaging system, and obtaining the at least one 2D X-ray image wherein at least three radiopaque fiducials of the registration phantom are detectable in each 2D image is implemented in an additional image acquisition after reconstructing the 3D medical image.

* * * * *